United States Patent
Kapalka et al.

(10) Patent No.: US 10,800,988 B2
(45) Date of Patent: Oct. 13, 2020

(54) METHOD FOR LIQUID AUTHENTICATION BY DETECTION OF FLAVONOID DERIVATIVES

(71) Applicant: SICPA HOLDING SA, Prilly (CH)

(72) Inventors: Agnieszka Kapalka, Prilly (CH); Xavier Urbaneja, Savigny (CH); Lucia Giovanola, Ivrea (IT); Paolo Schina, Turin (IT); Silvia Baldi, Samone (IT); Irma Disegna, Ivrea (IT); Silvano Tori, Ivrea (IT)

(73) Assignee: SICPA HOLDING SA, Prilly (CH)

( * ) Notice: Subject to any disclaimer, the term of this patent is extended or adjusted under 35 U.S.C. 154(b) by 743 days.

(21) Appl. No.: 15/516,013

(22) PCT Filed: Sep. 25, 2015

(86) PCT No.: PCT/EP2015/072109
§ 371 (c)(1),
(2) Date: Mar. 30, 2017

(87) PCT Pub. No.: WO2016/050636
PCT Pub. Date: Apr. 7, 2016

(65) Prior Publication Data
US 2017/0298283 A1    Oct. 19, 2017

(30) Foreign Application Priority Data
Sep. 30, 2014 (EP) .................................. 14003374
Mar. 18, 2015 (EP) .................................. 15159701

(51) Int. Cl.
*B01J 19/00* (2006.01)
*C07D 311/30* (2006.01)
(Continued)

(52) U.S. Cl.
CPC ........... *C10L 1/003* (2013.01); *B01J 19/0093* (2013.01); *B01L 3/5027* (2013.01);
(Continued)

(58) Field of Classification Search
CPC .......... B01J 19/0093; B01J 2219/00783; B01J 2219/0084; B01J 2219/00853;
(Continued)

(56) References Cited

U.S. PATENT DOCUMENTS 5,984,983 A    11/1999  Asgaonkar et al.
6,312,480 B1 *  11/2001  Jakob ...................... C10L 10/06
                                                             44/412
(Continued)

FOREIGN PATENT DOCUMENTS

| CN | 102993148 | 3/2013 |
| JP | 2006337221 | 12/2006 |
| WO | 2008086897 | 7/2008 |

OTHER PUBLICATIONS

Hermosin-Gutierrez et al. (I. Hermosin-Gutierrez, N. Castillo-Munoz, S. Gomez-Alonso, E. Garcia-Romero, Flavonol profiles for grape and wine authentication, In: "Cellulose Solvents: For Analysis, Shaping and Chemical Modification", Jan. 1, 2011 (Jan. 1, 2011), American Chemical Society, Washington, DC. (Year: 2011).*

(Continued)

*Primary Examiner* — Jennifer Wecker
(74) *Attorney, Agent, or Firm* — Muncy, Geissler, Olds & Lowe, P.C.

(57) ABSTRACT

A Liquid, comprising an hydrophobic flavonoid derivative electrochemically non-active, that is capable of restoring its electrochemical activity, the concentration of the flavonoid derivative being 10 ppm by weight or less, and an organic substance in an amount of 90% by weight or more.

19 Claims, 5 Drawing Sheets

(51) Int. Cl.
*C10L 1/00* (2006.01)
*C10L 1/18* (2006.01)
*G01N 33/22* (2006.01)
*C10L 1/185* (2006.01)
*C10L 1/28* (2006.01)
*G01N 27/416* (2006.01)
*C07D 311/62* (2006.01)
*B01L 3/00* (2006.01)
*C10L 1/19* (2006.01)

(52) U.S. Cl.
CPC .......... *C07D 311/30* (2013.01); *C07D 311/62* (2013.01); *C10L 1/18* (2013.01); *C10L 1/1855* (2013.01); *C10L 1/1857* (2013.01); *C10L 1/28* (2013.01); *G01N 27/416* (2013.01); *B01J 2219/0084* (2013.01); *B01J 2219/00783* (2013.01); *B01J 2219/00853* (2013.01); *B01J 2219/00873* (2013.01); *B01J 2219/00885* (2013.01); *B01J 2219/00889* (2013.01); *B01L 2300/0636* (2013.01); *B01L 2300/0645* (2013.01); *B01L 2300/0883* (2013.01); *B01L 2300/1827* (2013.01); *C10L 1/1905* (2013.01); *C10L 2230/16* (2013.01); *C10L 2290/38* (2013.01); *C10L 2290/60* (2013.01); *G01N 33/22* (2013.01)

(58) Field of Classification Search
CPC .... B01J 2219/00873; B01J 2219/00885; B01J 2219/00889; B01L 2300/0636; B01L 2300/0645; B01L 2300/0883; B01L 2300/1827; B01L 3/5027; C07D 311/30; C07D 311/62; C10L 1/003; C10L 1/18; C10L 1/1855; C10L 1/1857; C10L 1/1905; C10L 1/28; C10L 2230/16; C10L 2290/38; C10L 2290/60; G01N 27/416; G01N 33/22
See application file for complete search history.

(56) References Cited

U.S. PATENT DOCUMENTS

| | | | |
|---|---|---|---|
| 6,699,384 B1 | 3/2004 | Lin et al. | |
| 2005/0260764 A1* | 11/2005 | Grigsby, Jr. | ....... G01N 21/6428 436/172 |
| 2007/0134172 A1* | 6/2007 | Buchholz | ................ A61P 17/06 424/59 |
| 2014/0120521 A1 | 5/2014 | Abi-Samra et al. | |

OTHER PUBLICATIONS

Isidro Hermosin-Gutierrez et al.: "Flavonol Profiles for Grape and Wine Authentication" In: "Cellulose Solvents: For Analysis, Shaping and Chemical Modification" Jan. 1, 2011 (Jan. 1, 2011), American Chemical Society, Washington, DC, XP055198980, ISSN: 0097-6156, ISBN: 978-0-84-120007-4 vol. 1081, pp. 113-129.
Allen J. Bard and Larry R. Faulkner (Authors), Electrochemical Methods: Fundamentals and Applications; ISBN-13: 978-0471043720.
A. C. Waiss et al.: "NMR Study of trimethylsilyl ethers of flavonoid compounds", Tetrahedron Letters, vol. 5, No. 10, Jan. 1, 1964 (Jan. 1, 1964), pp. 513-518, XP055227414, GB ISSN: 0040-4039.
Keizo Hayashiya: "Studies on Flavonoid. Part V", Nippon Nogei Kagakukaishi—Journal of the Agricultural Chemical Society of Japan, vol. 33, No. 12, Jan. 1, 1959 (Jan. 1, 1959), pp. 1065-1068, XP055227473, JP ISSN: 0002-1407 (and English language translation).
W. Greene, P. G. M. Wuts, *Protective Groups in Organic Synthesis*, Wiley-Interscience, New York, Third Edition, 1999, 229 pages.
W. Greene, P. G. M. Wuts, *Protective Groups in Organic Synthesis*, Wiley-Interscience, New York, Fifth Edition, 2014, 873 pages.
Pavel Hanustiak et al.: "Electrochemical Behaviour of Flavonoids on a Surface of a Carbon Paste Electrode", Biomed. Papers, Jan. 1, 2005 (Jan. 1, 2005), XP055243195, abstract, pp. 44-47.
International Search Report and Written Opinion issued with respect to application No. PCT/EP2015/072109.
Eurasian office action in counterpart Eurasian Application No. 201690362/28 dated Dec. 26, 2016 (and English language translation).

* cited by examiner

METHOD FOR LIQUID AUTHENTICATION BY DETECTION OF FLAVONOID DERIVATIVES

TECHNICAL FIELD

The technical field of the present invention is a method for the detection of reactive molecules, specifically flavonoid derivatives in a liquid environment. These reactive molecules can act as marker for the liquid, serving as authentication means for verifying the authenticity and/or origin of the liquid. The present invention further concerns liquids, in particular fuels comprising a flavonoid derivative marker, the use of flavonoids as a marker for authentication purposes, authentication methods using the marker, and corresponding authentication equipment and devices. The present invention further provides novel compounds useful as markers in liquids, such as fuels.

BACKGROUND OF THE INVENTION

In many instances it is desired to be able to verify the origin and authenticity of liquids of various kinds, such as fuels (e.g. diesel, kerosene, gasoline etc.) in order to be able to identify forged or non-genuine products. For this purpose, a marking substance (marker) is often added to the liquid, such as a specific dye. The addition of a marker is also employed in order to distinguish between liquids that are chemically identical or very similar, but which are regulated differently. One example is the addition of a certain dye into heavily taxed diesel fuel in Germany, while the chemically very similar or identical heating oil is taxed at a lower rate and is not marked with a specific dye. The identity of a liquid in a car tank can then be assessed by analyzing the liquid as to presence of the specific marker dye.

The authenticity of the liquid is then assessed by means of a detector, e.g. a colour detector or spectral analysis in case of a certain dye. Yet, often bulky and expensive equipment is needed in order to detect such a marker. Further, the marker often needs to be present in significant quantities in order to allow a reliable detection.

In another aspect, the marking can be easily counterfeited in case that commercially available substances (e.g. dyes) are used, as only the properties of the marker (but not its interaction with a detection device) are assessed. Further, in cases of optical markers such as dyes, their presence can be easily determined, sometimes even with the naked eye. Such a maker therefore provides only a very low level of security, as a counterfeiter can easily assess which kinds of visible markers are present, and can then try to get a similar optical effect by using similar or commercially available substances for addition to a forged product.

It would therefore be desirable to have a marker substance that is difficult to detect by the naked eye. Further, such a marker is preferably chemically similar to the liquid in which it is used, but can still be detected even when present only in small quantities. Of course, such a maker should not naturally occur in the liquid to be marked.

SUMMARY OF THE INVENTION

In view of the above, it is an object of the present invention to provide a method for authenticating the origin and/or authenticity of a liquid that overcomes the problems of the prior art. A further object is to provide a method for authenticating the origin and/or authenticity of a liquid that cannot be performed with the naked eye, but which can still be performed on-site with comparatively simple and compact equipment, such as hand-held devices.

It is a further object of the present invention to provide a marker that can be easily detected even in small quantities with such equipment. The marker should also be easy to obtain and to produce in an environmentally friendly manner.

Also, the present invention aims at providing a liquid having an improved security level, i.e. which is more difficult to counterfeit, than liquids containing a conventional marker. The present invention further aims at providing a marker that is useful in such methods and for such purposes.

The mentioned problems are solved by the subject-matter of the independent claims. Further preferred embodiments are defined the dependent claims and are also described below.

The present invention provides inter alia the following
1. A liquid, comprising
   a) a flavonoid derivative obtainable by modifying the hydroxyl groups of a flavonoid with organic groups, the concentration of the flavonoid derivative being 100 ppm by weight or less, and
   b) an organic substance in an amount of 90% by weight or more.
2. The liquid according to item 1, wherein the liquid is a fuel and the organic substance is present in an amount of equal to or greater than 95% by weight and is one or more hydrocarbons having 6 to 22 carbon atoms, methanol or ethanol.
3. The liquid according to item 1 or 2, wherein the hydrophobic flavonoid derivative loses some or all of the modifying organic groups upon heating to a temperature of 50° C. or higher.
4. The liquid according to any one of items 1 to 3, wherein the flavonoid derivative obtainable by modifying the hydroxyl groups of a flavonoid with organic groups is represented by any of the following formulae:

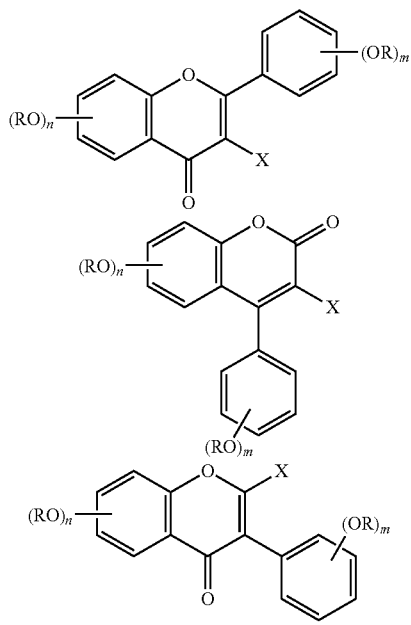

where X represents H or OR;

n represents an integer of 0 to 4, and m represents an integer of 0 to 5, provided the sum of m and n is 2 or more, preferably three or more, more preferably 4 or more, such as 5, 6, 7, or 8, but preferably 7 or less, more preferably 6 or less.

several R in one molecule can be the same or different, and each R can be

H, a branched, linear or cyclic alkyl group having 1 to 50, preferably 2 to 30 carbon atoms, more preferably 3 to 15 carbon atoms, a C(=O)-alkyl group, wherein the alkyl group is defined as above, a trialkylsilyl group wherein the alkyl groups each are independently a branched, linear or cyclic alkyl group having 1 to 50, preferably 2 to 30 carbon atoms, more preferably 3 to 15 carbon atoms, a diarylalkylsilyl group having two aryl groups and one alkyl group wherein the alkyl group is a branched, linear or cyclic alkyl group having 1 to 50, preferably 2 to 30 carbon atoms, more preferably 3 to 15 carbon atoms, and the aryl groups are each independently aromatic rings having 6 to 10 carbon atoms, and preferably both aryl groups are phenyl groups, a dialkylarylsilyl group having one aryl group and two alkyl groups, wherein the alkyl groups and the aryl groups are defined as above for the diarylalkylsilyl group, an allyl group, a methylene alkylether group wherein the alkyl group is defined as above, or a tetrahydropyranyl group, with the proviso that at least one of the R groups does not represent hydrogen.

5. Use of a flavonoid derivative obtainable by modifying the hydroxyl groups of a flavonoid with organic groups as an authenticating marker in a liquid, preferably a fuel.

6. Use according to item 5, wherein the flavonoid derivative is as defined in item 4.

7. A method for authenticating the genuineness and/or origin of a liquid containing a flavonoid derivative obtainable by derivatizing the hydroxyl groups of a flavonoid with organic groups, comprising the steps of mixing said liquid containing the flavonoid derivative with an electrolytic solution to produce a mixture;

heating and then cooling the mixture to change the electrochemical activity and to produce an electrochemically more active flavonoid or flavonoid derivative;

separating said obtained electrochemically more active flavonoid or flavonoid derivative from the mixture, and electrochemical analysis of the obtained electrochemically more active flavonoid or flavonoid derivative.

8. The method according to item 7, wherein the liquid is a fuel and wherein the concentration of the marker is equal to or less than 10 ppm by weight.

9. The method according to any one of items 7 and 8, wherein the method is implemented in a portable device.

10. The method according to any one of items 7 to 9, wherein the separation of the obtained electrochemically more active flavonoid or flavonoid derivative from liquid is obtained with a flow side by side in a mixing channel where also the solution comprising one or more reagents capable of fully or partially de-derivatize the flavonoid derivative is flowing.

11. The method according to any one of items 7 to 10, which is performed in a lab-on-chip detection device.

12. The liquid according to any one of items 1 to 4, use according to items 5 or 5 or the method according to any one of items 7 to 12, wherein the flavonoid derivative obtainable by modifying the hydroxyl groups of a flavonoid with organic groups contains a structural unit derived from quercetin or morin.

13. A detection device configured to de-derivatize a flavonoid derivative dissolved in a liquid and to separate said flavonoid from said liquid, preferably a fuel, comprising:

a reaction chamber (100) for holding a reactant and for receiving said liquid;

a first entry (101) and a microfluidic channel for introducing an amount of said liquid into the reaction chamber (100);

a heater (104) for heating up the reaction chamber (100) to a reaction temperature;

an electrolytic solution chamber for holding an electrolytic solution;

a second entry (102) for introducing an amount of said electrolytic solution into the electrolytic solution chamber (100);

a mixing channel (110) configured to establish a laminar side-by-side flow of the mixture of said liquid and reactant from the reaction chamber (100) and the electrolytic solution from the electrolytic solution chamber; and a detection chamber (120) arranged at the end of said mixing channel (110) and having electrodes for electrochemical analysis.

14. The detection device of item 13, wherein the device further comprises an active cooling element for cooling said reaction chamber (100).

15. The detection device of item 13 or 14, wherein the detection chamber (120) comprises hydrophilic surface.

16. The detection device of any one of items 13 to 15, wherein the detection chamber (120) comprises a working electrode (122), a counter electrode (121), and a reference electrode (123).

17. The detection device of item 16, wherein the working electrode (122) comprises a microelectrode array.

18. The detection device of any one of items 13 to 17, further comprising a controller configured to control fluid flow and temperature for performing a method of any one of items 7 to 12.

19. A system comprising a detection device according to any one of items 13 to 18, a liquid, preferably a fuel; and a flavonoid derivative obtainable by modifying the hydroxyl groups of a flavonoid with organic groups dissolved in the fuel with a concentration of equal to or less than 10 ppm by weight, more equal to or less than 1 ppm by weight.

20. The system according to item 19, wherein the flavonoid derivative contains a structural unit derived from quercetin or morin.

21. A flavonoid derivative represented by any of the following formulae:

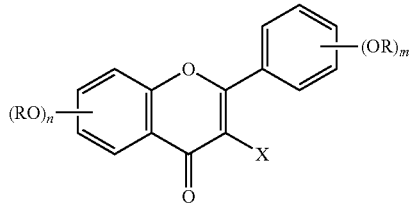

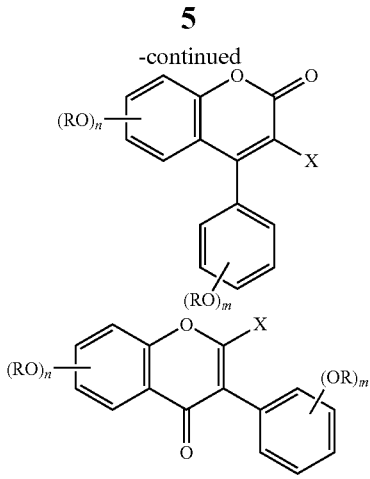

where X represents H or OR, n represents an integer of 0 to 4, and m represents an integer of 0 to 5, provided the sum of m and n is 2 or more, preferably three or more, more preferably 4 or more, such as 5, 6, 7, or 8, but preferably 7 or less, more preferably 6 or less.

several R in one molecule can be the same or different, and each R can be

H, a branched, linear or cyclic alkyl group having 1 to 50, preferably 2 to 30 carbon atoms, more preferably 3 to 15 carbon atoms, a C(=O)-alkyl group, wherein the alkyl group is defined as above, a trialkylsilyl group wherein the alkyl groups each are independently a branched, linear or cyclic alkyl group having 1 to 50, preferably 2 to 30 carbon atoms, more preferably 3 to 15 carbon atoms, diarylalkylsilyl group having two aryl groups and one alkyl group wherein the alkyl group is a branched, linear or cyclic alkyl group having 1 to 50, preferably 2 to 30 carbon atoms, more preferably 3 to 15 carbon atoms, and the aryl groups are each independently aromatic rings having 6 to 10 carbon atoms, and preferably both aryl groups are phenyl groups, an dialkylarylsilyl group having one aryl group and two alkyl groups, wherein the alkyl groups and the aryl groups are defined as above for the diarylalkylsilyl group, an allyl group, methylene alkylether group wherein the alkyl group is defined as above, or a tetrahydropyranyl group, with the proviso that at least of the R groups does not represent hydrogen.

22. The flavonoid derivative according to item 21, which is represented by any of the following formulae (A) and (B)

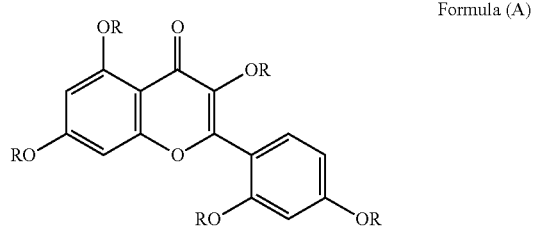

Formula (A)

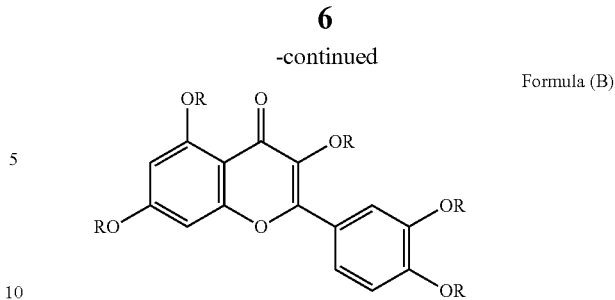

Formula (B)

wherein the R groups in formula (A) and (B) can be the same or different and are selected from the meanings of R as defined in item 21.

23. The flavonoid derivative according to item 21 or item 22, wherein all R groups are the same and are one member selected from the group consisting of acetyl, trialkylsilyl, diarylalkylsilyl and dialkylarylsilyl.

Embodiments of the present invention utilize a specific derivatization of electrochemically active compounds (preferably polyphenolics, flavonoids) to render them soluble in petroleum products (e.g. fuel). The derivatives are electrochemically non-active, in particular in comparison to the respective flavonoids and polyphenols, and can thus be regarded as a latent marker. They further provide a security feature for liquids, in particular hydrocarbon fuels, as they are resistant to potential fuel laundering.

The latent marker (flavonoid derivative) can then be detected and analyzed in a Lab-on-a-chip (MEMS, μ-TAS) device. The device performs a sample extraction, followed by a specific chemical reaction to release partially or completely the modifications introduced in the original flavonoid structure by the derivatization, to thereby restore the electrochemical activity. Electrochemical detection of flavonoid in a Lab-on-chip (LOC) coupled with a potentiostat and optionally a smartphone then allows the qualitative and quantitative analysis of the liquid as to presence and amount of the marker, respectively the flavonoid obtained therefrom.

DETAILED DESCRIPTION

Figure 1:
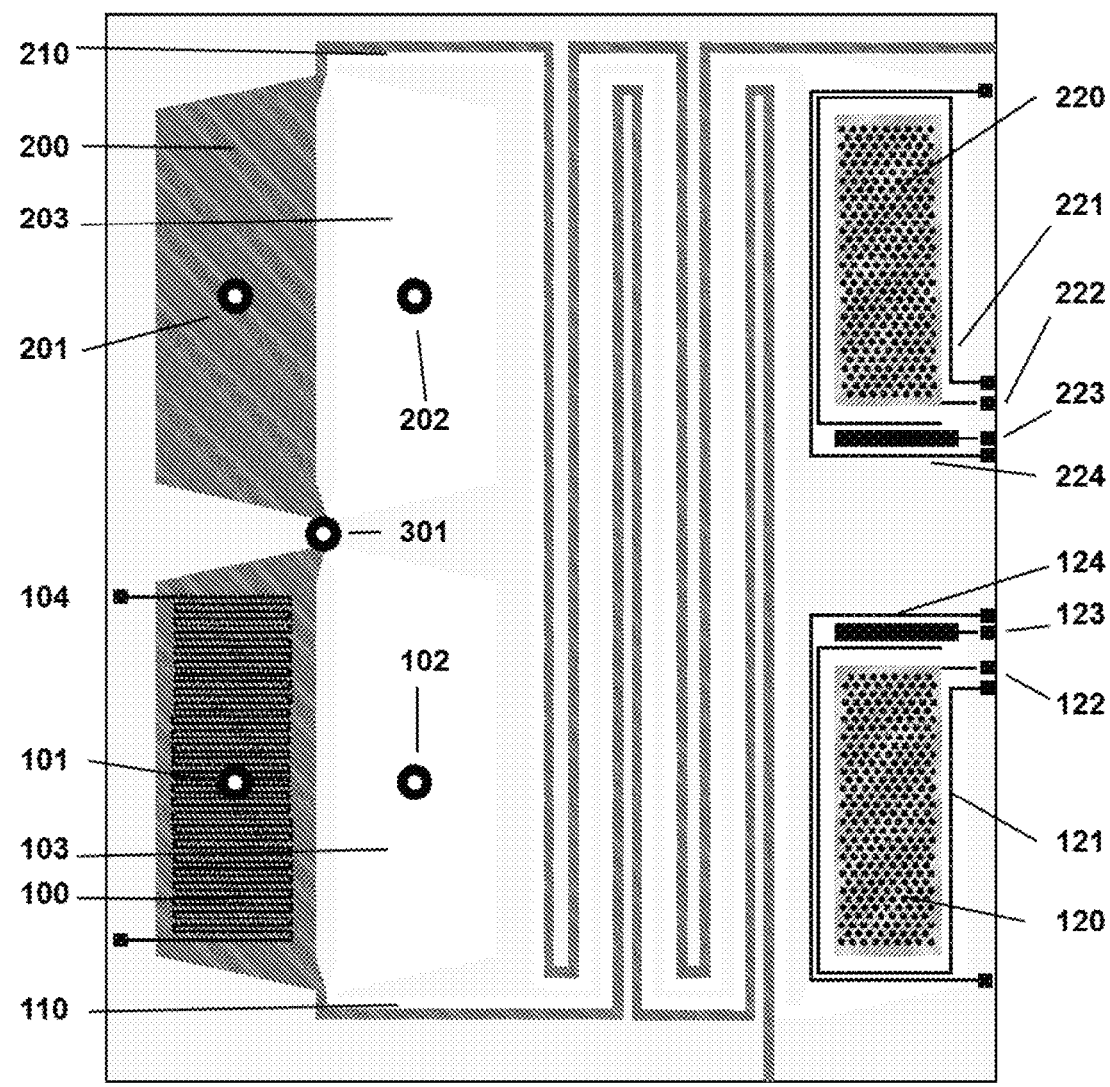
FIG. 1 shows a first embodiment of a design of a reaction chamber LOC.

The term "liquid" is used to denote a substance that is liquid at room temperature (20° C.) and 1 atm pressure. The liquid is preferably a fuel. The term "fuel" is used to denote liquid compositions preferably consisting essentially of (i.e. more than 95% by weight) of hydrocarbons. Examples of fuels include diesel, gasoline, kerosene, liquefied petroleum gas (LPG), and other fuel oils such as naptha. Although not a hydrocarbon fuel in the strict sense, the term "fuel" in the present invention also encompasses methanol and in particular ethanol.

The term "organic" has its common meaning in the art. An organic group is therefore a group that is part of organic chemistry, and as such has at least one carbon atom and typically at least one hydrogen atom. In a more narrow and preferred definition, an organic substance and an organic group are composed to at least 25% by weight or more of hydrogen and carbon atoms, more preferably at least 50% by weight, and up to 100% by weight. The remainder may be made of any species, but preferably consists of atoms selected from the group of oxygen, nitrogen, silicon, sulfur and halogen (F, Cl, Br, I) atoms, more preferably selected from the group consisting of oxygen, nitrogen, silicon and halogens, and further preferably selected from the group consisting of oxygen, nitrogen and silicon.

The term "comprising" is open-ended and allows for the presence of further components that are not explicitly recited. Yet, the term "comprising" also encompasses the more restrictive meanings "consisting of" and "consisting essentially of", so that further components other than those explicitly recited may be completely or substantially absent.

The term "one or more" is used to denote that at least one of the following materials or elements is present. Typically, the term is used to denote the presence of one, two, three, four, five or six of the respective materials or elements, more preferably one, two or three, further preferably one or two.

In the following specification, all physical properties refer to those measured at standard conditions (20° C., 1 atm pressure).

The elements and materials used in the present invention will now be described.

Marker

The marker used in the liquid for authenticating the origin and/or authenticity of the liquid is a flavonoid (polyphenol) derivative. The marker is preferably electrochemically non-active, in particular in comparison to the fully or partially de-derivatized flavonoid that is detected in the use and the processes of the present invention. The marker is thus preferably used as a latent marker, which reveals the properties attributed to the authenticity of the liquid only after a chemical reaction, since the partially or fully de-derivatized reaction product obtained from the marker is the species that is in fact detected and/or analyzed. As the marker is indicative for the authenticity and/or origin of a liquid, the marker is typically a compound that is prepared separately and added to the liquid on purpose. Put differently, the marker is typically not a compound that is naturally occurring in the liquid to be tested for its authenticity.

The species that is in fact detected is a Flavonoid or a less derivatized flavonoid derivative, which is generated from a flavonoid derivate present in the liquid during or prior to the detection/authentication process. Flavonoids are natural polyphenolic compounds of plant origin. They are electro-chemically active, which means that they can undergo oxidation and reduction reactions in an electrochemical process. The authentication method of the present invention relies on this electrochemical process and utilizes the reaction kinetics (such as the oxidation potential, the necessary current or the speed of the reaction) for authentication purposes, which will be explained in more detail below.

To date, more than 5000 structures of naturally occurring flavonoids have been identified. Their common natural sources are mainly different source of fruits, vegetables and cereals (examples include black or green tea, blueberries, red wine, parsley, onions, etc)

The chemical structure of flavone is presented below.

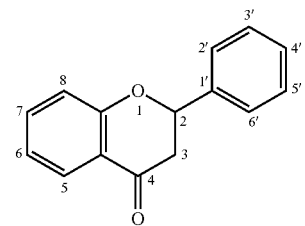 [SMILES: O=C1CC(c2ccccc2)Oc2ccccc21]

Flavonoids are derived from this heterocyclic oxygen compound flavone and its related forms isoflavone and neoflavone. In a flavonoid, all three rings are typically substituted by hydroxyl groups and/or methoxy groups, and particular forms differ mainly in the degree of substitution and oxidation.

Derivatization of Flavonoids

The marker used in the present invention is a flavonoid derivative, wherein a hydrophilic group (a hydroxyl group) of a flavonoid is reacted with a reagent that introduces a hydrophobic moiety at the respective position, thereby forming a flavonoid derivative wherein the hydrophilic (hydroxyl) group is converted into a more hydrophobic group. The hydrophilic (hydroxyl) group is then restored in the detection process, and the presence of the flavonoid is detected utilizing an electrochemical process.

These derivatives present in the liquid can be obtained by derivatizing synthetic or naturally occurring flavonoids, as well known to the skilled person.

The derivatization of the hydrophilic groups (hydroxyl groups) of a flavonoid with hydrophobic molecules is performed in order to increase their solubility and stability in fuel. This specific derivatization makes the obtained flavonoid derivatives more resistant to fuel laundering processes (e.g., chemical attack with strong acids, bases etc) and render it electrochemically less reactive in comparison to the non-derivatized flavonoid (latent marker).

The preferred markers used in the present invention are flavonoid derivatives that can be obtained from flavonoids having the following basic structures:

(i) Flavonoids, derived from flavone:

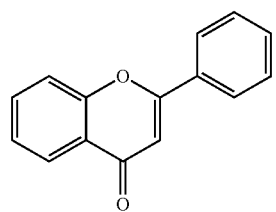 [SMILES: O=c1cc(-c2ccccc2)oc2ccccc12]

(ii) Isoflavonoids, derived from isoflavone (3-phenyl-chromen-4-one; 3-phenyl-1,4-benzopyrone):

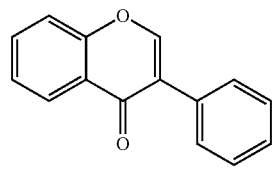 [SMILES: O=c1c(-c2ccccc2)coc2ccccc12]

(iii) Neoflavonoids, derived from neoflavone (4-phenylcoumarine (4-phenyl-1,2-benzopyrone)):

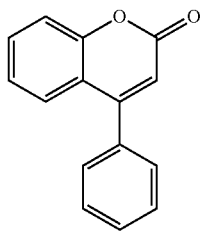 [SMILES: O=c1cc(-c2ccccc2)c2ccccc2o1]

In a flavonoid, all three rings are typically substituted by hydroxyl groups and/or methoxy groups. The markers (flavonoid derivatives) used in the present invention are thus preferably those according to any one of the following formulae:

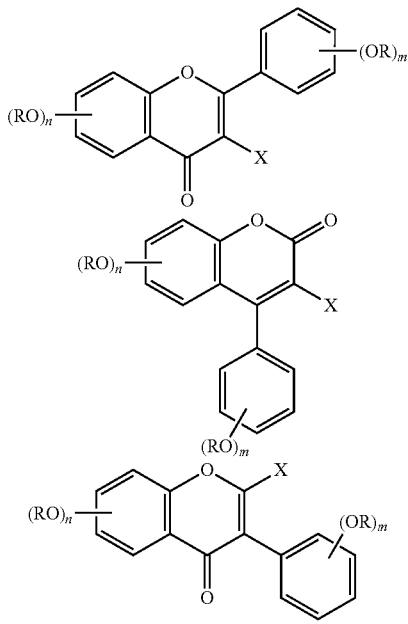

where
X represents H or OR, preferably OR,
n represents an integer of 0 to 4, and m represents an integer of 0 to 5, provided the sum of m and n is 2 or more, preferably 3 or more, more preferably 4 or more, such as 5, 6, 7, or 8, but preferably 7 or less, more preferably 6 or less.

Several R in one molecule can be the same or different, and each R can be H,
a branched, linear or cyclic alkyl group having 1 to 50, preferably 2 to 30 carbon atoms, more preferably 3 to 15 carbon atoms,
a C(=O)-alkyl group, wherein the alkyl group is defined as above,
a trialkylsilyl group wherein the alkyl groups each are independently a branched, linear or cyclic alkyl group having 1 to 50, preferably 2 to 30 carbon atoms, more preferably 3 to 15 carbon atoms,
diarylalkylsilyl group having two aryl groups and one alkyl group wherein the alkyl group is a branched, linear or cyclic alkyl group having 1 to 50, preferably 2 to 30 carbon atoms, more preferably 3 to 15 carbon atoms, and the aryl groups are each independently aromatic rings having 6 to 10 carbon atoms, and preferably both aryl groups are phenyl groups,
an dialkylarylsilyl group having one aryl group and two alkyl groups, wherein the alkyl groups and the aryl groups are defined as above for the diarylalkylsilyl group,
an allyl group, methylene alkylether group wherein the alkyl group is defined as above, or a tetrahydropyranyl group., with the proviso that at least one of the R groups does not represent H. Preferably two or more of the R-groups, if present, do not represent H.

Further groups represented by R can be known protective groups for a hydroxyl group, forming together with the oxygen to which R is bound e.g, a Methoxymethyl ether, allyl ether, benzyl ether, butyldiphenylsilylether, triphenylsilylether, triisopropylsilylether, acetyl, tosyl group or benzoid acid ester. Such protective groups are well known to the skilled person and listed for instance in W. Green, P. G. M. Wuts, Protective Groups in Organic Synthesis, Wiley-Interscience, New York, 1999, 76-86, 708-711. Preferred groups represented by R are tert-butyldimethylsilyl, tert-butyldiphenylsily, tert-butyl and isopropyl.

As the compounds used as marker are flavonoid derivatives, it is a requirement that at least one of the groups represented by R is not H. Preferably two or more, and more preferably three or more, such as 4 or 5, of the groups represented by R are not hydrogen, of course provided that there are at least three or more, such as 4 or 5, groups represented by R (i.e. provided that the sum of n and m is 2 or more, or 3 or more, such as 4 or 5, respectively).

In one embodiment, none of the R groups represents an alkyl group. In another embodiment, none of the R groups forms, together with the O to which it is connected, a fatty acid ester residue.

In one embodiment, the present invention provides novel compounds that are useful as markers in liquids, such as fuels, as described above. In one embodiment, the compounds are morin derivatives selected from those represented by the following formula (A), and quercetin derivatives, represented by the following formula (B):

Formula (A)

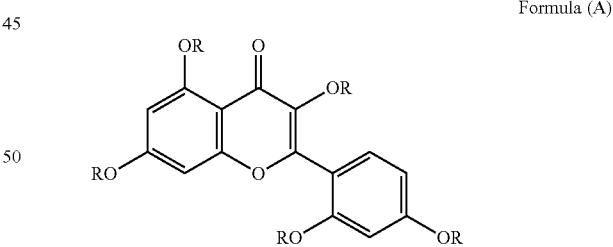

Formula (B)

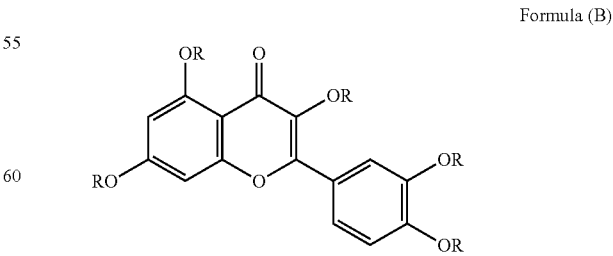

Herein, R is as defined above. Preferably, three or four of the R groups in formulae (A) and (B) are not hydrogen, and are identical groups other than hydrogen selected from the meanings of R described above. For example, it is in one embodiment preferred that three or four of the R groups are all acetyl (—C(O)CH3) or are all triisopropylsilyl (TIPS, —Si[CH(CH$_3$)$_2$]$_3$).

In one preferred embodiment of formula (A), four of the five R groups are identical and are each either acetyl or a silyl group, which is preferably selected from triisopropylsilyl and diphenyl t-butyl silyl, and in one preferred embodiment of formula (B) four of the five R groups are identical and are each acetyl. In these embodiments, the sole remaining R group that is not either acetyl or triisopropylsilyl, or that is not acetyl, respectively, is preferably H. The R group that is not either acetyl or triisopropylsilyl, or that is not acetyl, respectively, and that is preferably H, is preferably the R present on the ring having only one OR group (the pyranon ring).

In one embodiment, none of the R groups represents an alkyl group. In another embodiment, none of the R groups forms, together with the O to which it is connected, a fatty acid ester residue.

The amount of the marker in the liquid is typically 100 ppm (by weight) or less, preferably 50 ppm (by weight) or less, and most preferably 10 ppm (by weight of less). It can however also be as low as 1 ppm or less. A suitable concentration can be determined by the skilled person by taking into account the sensitivity of the authentication equipment to be used, the ease of removal of derivatizing groups therein, the used de-derivatizing agents and the electrochemical reactivity of the obtained species.

PROCEDURES FOR OBTAINING FLAVONOID DERIVATIVES—EXAMPLES

The skilled person is well aware of the chemistry that can be used for transforming a hydroxyl group of a flavonoid e.g. into a group of formula OR as defined above. Such methods can be used in the present invention without limitation. Merely for illustrative purposes, the following Procedures 1-6 describe specific processes, which are not intended to limit the present invention in any way:

Procedure 1

In a round-bottomed flask, a flavonoid compound is dissolved in a suitable solvent, such as DMF (dimethylformamide). To this solution, t-BuPh$_2$SiCl and imidazole are slowly added at room temperature. The reaction mixture is stirred for a suitable time, e.g. 3 h, keeping the same temperature. The flavanoid derivative thus formed is isolated from the reaction mixture, e.g. by adding a saturated solution of NaCl in water to the reaction mixture and then extracting the flavonoid derivative using for instance petrol ether.

Procedure 2

To a solution of flavonoid and Isobutylene in CH$_2$Cl$_2$, concentrated H$_2$SO$_4$ is added dropwise. The reaction mixture is stirred at 25° C. for 8 h, followed by addition of water. The flavonoid is extracted with petrol ether and can be used without further purification.

Procedure 3

Flavonoid and t-Butyl chloride are added respectively to pyridine at 25° C. The reaction is stirred for 4 h. Then, the reaction mixture is carefully poured onto an aqueous solution of 2M HCl. The desired d flavonoid derivative is obtained by extraction with a suitable solvent such as petrol ether.

Procedure 4

In a round-bottomed flask, flavonoid compound, Me$_2$CHBr and K$_2$CO$_3$ are dissolved in acetone at 20° C. The reaction is allowed to stir for 19 h. Then, the solvent is removed under vacuum, and water is added to the crude reaction mixture. The desired flavonoid derivative can then be extracted by adding a suitable solvent, such as petrol ether.

Procedure 5

In a round-bottomed flask, a flavonoid compound, TIPSCl (tri-isopropylsilyl chloride), and imidazole are dissolved in dichloromethane at room temperature. The reaction is allowed to stir for 24 h. Then, the solvent is removed under vacuum, and water is added to the reaction crude. The flavonoid derivative can then be obtained by extraction with a suitable solvent, such as petrol ether.

Procedure 6

In a round-bottomed flask, a flavonoid compound, acetic acid anhydride and triethylamine are dissolved in dichloromethane at room temperature. The reaction is allowed to stir for 3 h. Then, the solvent is removed under vacuum, and water is added to the reaction crude. The desired flavonoid derivative can be obtained by extraction with a suitable solvent, such as petrol ether.

The starting material flavonoids can be obtained by routine technology, and many are commercially available. As one Example, flavonoid derivatives can be obtained using Quercetin (CAS Number 117-39-5) as starting material:

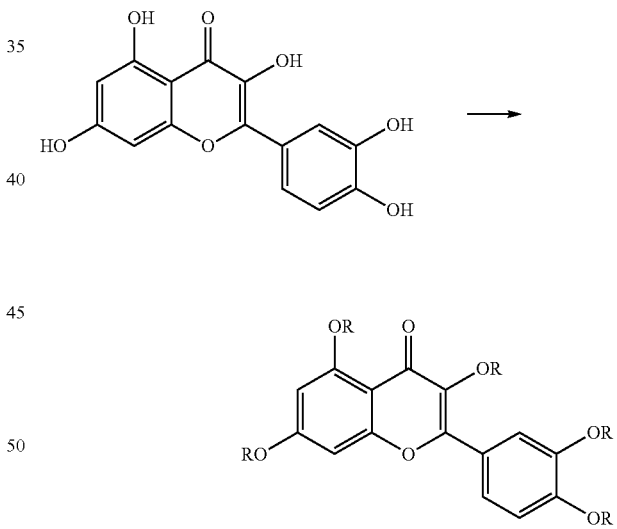

Another commercially available flavonoid used as starting material is Morin hydrate (CAS Number 654055-01-3)

The following Examples describe the synthesis of some specific flavonoid derivatives that are preferably used as marker in the present invention.

Example 1

Using one of the procedures described above, the quercetin derivative (3,5,7-tri-tert-butoxy-2-(3,4-di-tert-butoxyphenyl)-4H-chromen-4-one) can be synthesized.

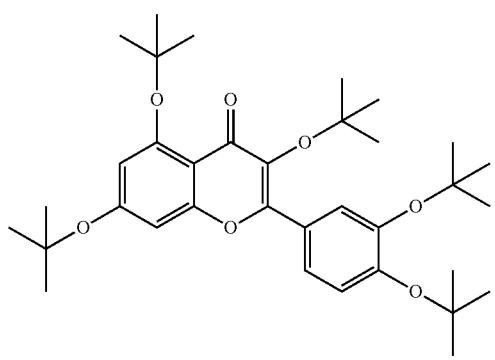 [SMILES: CC(C)(C)Oc1cc(OC(C)(C)C)c2c(=O)c(OC(C)(C)C)c(-c3ccc(OC(C)(C)C)c(OC(C)(C)C)c3)oc2c1]

Specific Chemical Information:

Chemical Formula: C35H50O7

Exact Mass: 582.36

Molecular Weight: 582.77 m/z: 582.36 (100.0%), 583.36 (38.7%), 584.36 (8.5%)

Elemental Analysis: C, 72.13; H, 8.65; O, 19.22

Example 2

Using one of the procedures described above, the quercetin derivative (2-(3,4-bis((tert-butyldiphenylsilyl)oxy)phenyl)-3,5,7-tris((tert-butyldiphenylsilyl)oxy)-4H-chromen-4-one) can be synthesized.

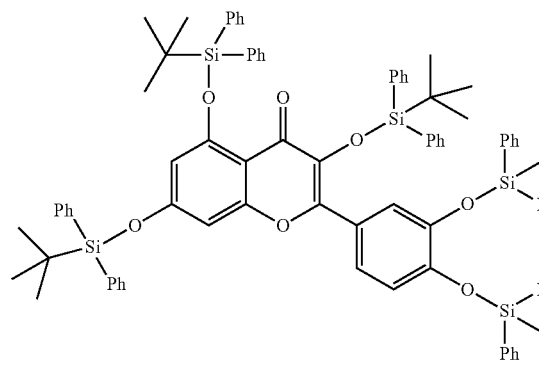

Specific Chemical Information:

Chemical Formula: $C_{95}H_{100}O_7Si_5$

Exact Mass: 1492.63

Molecular Weight: 1494.23 m/z: 1493.63 (100.0%), 1492.63 (78.0%), 1494.64 (43.3%), 1494.63 (35.4%), 1495.64 (26.4%), 1495.63 (18.4%), 1496.64 (16.0%), 1496.63 (4.2%), 1497.64 (4.1%), 1497.63 (2.6%), 1498.64 (1.3%), 1493.64 (1.1%)

Elemental Analysis: C, 76.36; H, 6.75; 0, 7.50; Si, 9.40

Example 3

Using one of the procedures described above, the quercetin derivative 2-(3,4-diacetoxyphenyl)-4-oxo-4H-chromene-3,5,7-triyl triacetate can be synthesized.

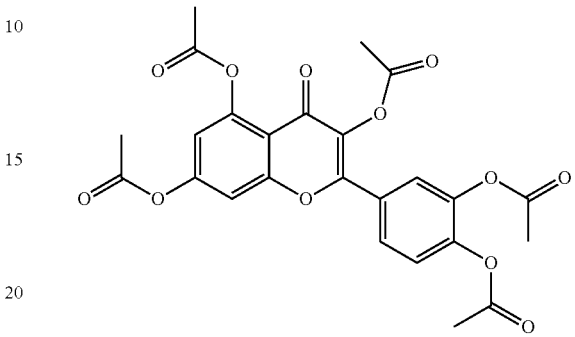

Specific Chemical Information:

Chemical Formula: C25H20O12

Exact Mass: 512.10

Molecular Weight: 512.42 m/z: 512.10 (100.0%), 513.10 (27.7%), 514.10 (6.1%)

Elemental Analysis: C, 58.60; H, 3.93; O, 37.47

Example 4

Using one of the procedures described above, the morin derivative 2-(2,4-diacetoxyphenyl)-4-oxo-4H-chromene-3,5,7-triyl triacetate can be synthesized.

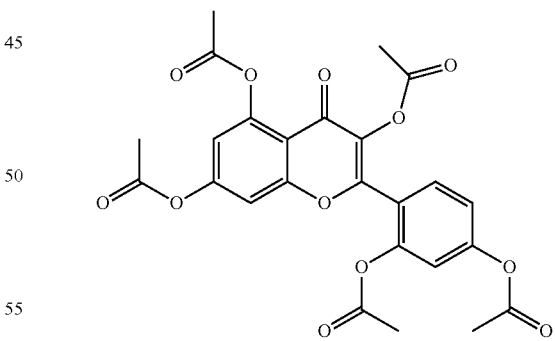

Specific Chemical Information:

Chemical Formula: C25H20O12

Exact Mass: 512.10

Molecular Weight: 512.42 m/z: 512.10 (100.0%), 513.10 (27.7%), 514.10 (6.1%)

Elemental Analysis: C, 58.60; H, 3.93; O, 37.47

Example 5

Using one of the procedures described above, the morin derivative containing four groups tri-isopropylsilyl (TIPS) can be synthesized.

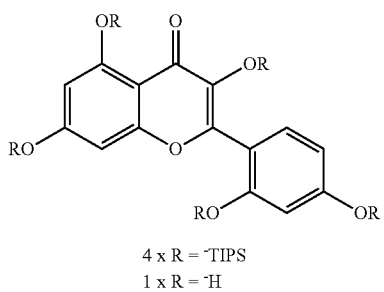

4 x R = ⁻TIPS
1 x R = ⁻H

Specific Chemical Information:
  Chemical Formula: C51H90O7Si4
  Exact Mass: 926.58
  Molecular Weight: 927.60
  m/z: 926.58 (100.0%), 927.58 (76.8%), 928.58 (29.5%), 928.57 (13.4%), 929.58 (12.6%), 930.58 (3.9%), 929.59 (3.0%), 929.57 (2.0%), 930.59 (1.2%)
  Elemental Analysis: C, 66.04; H, 9.78; O, 12.07; Si, 12.11

All prepared compounds were tested for their solubility in a solvent mixture containing 76% iso-octane, 16% toluene, 5% TBME, 3% EtOH, which is representative for a fuel. All components could be dissolved in an amount of at least 10 ppm.

Restoration of the Electrochemical Activity of Flavonoid

For detecting the presence of a maker in a liquid to be analyzed, the marker is then again transformed to the flavonoid by removing some, and preferably all of the modification groups (protective groups). This means for the flavonoid deriviatives described above that some or all of the R groups are transformed to hydrogen, so that a partially or fully de-derivatized species is formed. Since the de-derivatized species or flavonoid is electrochemically more active in comparison to the flavonoid derivative used as the marker, the detection of the de-derivatized species or flavonoid can be performed electrochemically.

For this purpose, it is possible to obtain the marker in the fuel and to convert it again to the more electrochemically active species, such as the flavonoid. This can be effected e.g. within a handheld device, such as a Lab-on-Chip (LOC). Within the LOC, a specific chemical reaction releases partially or completely the modifications introduced in the flavonoid structure in order to restore its electrochemical activity and enable the electrochemical detection. Preferably, the de-derivatized species or flavonoids precipitate during the process, i.e., separate from fuel components, due to the increased hydrophilicity of the de-derivatized species or flavonoid compared to the less hydrophilic flavonoid derivative.

As illustrative methods for obtaining the partially de-derivatized, more electrochemically active species or fully de-derivatized flavonoid from the marker (the flavonoid derivative), the following four possible procedures to restore electrochemical activity of the marker in a reaction chamber of LOC can be used, as presented in FIGS. 1-4:

Procedure 1

In a reaction chamber, a derivatized flavonoid (shown in example 2) undergoes a chemical reaction in the presence of suitable reagents: a base (e.g. K₂CO₃, Kryptofix 222 (4,7,13,16,21,24-Hexaoxa-1,10 diazabicyclo[8.8.8]hexacosane), and a solvent such as CH₃CN. Under suitable reaction conditions, such as at a temperature of 55° C.; the structure modification is removed in short time (e.g. 10 minutes or less), resulting in formation of the flavonoid:

Procedure 1:

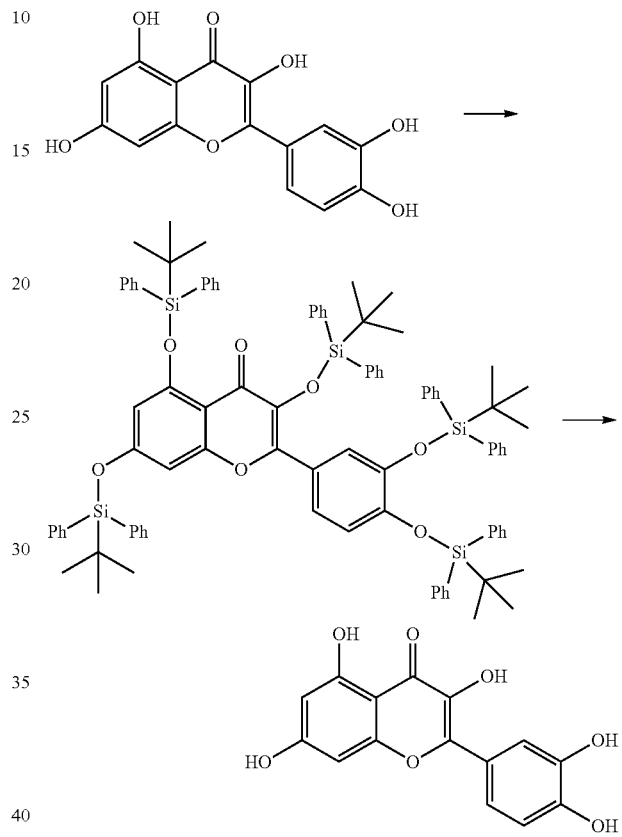

Procedure 2

In a reaction chamber, a flavonoid derivative (as shown for instance in example 1) undergoes a chemical reaction in the presence of suitable reagents: anhydrous CF₃CO₂H; at a suitable temperature of e.g. 25° C., over as suitable time, such as during 5 min, resulting in release of structure modification.

Procedure 3

In a reaction chamber, a flavonoid derivative (e.g. as shown in example 1) undergoes a chemical reaction in the presence of reagents: CF₃CH₂OH, CF₃SO₃H; at the temperature of e.g. −5° C., over a time of e.g. 1 min, resulting in release of structure modification.

Procedure 2 and 3:

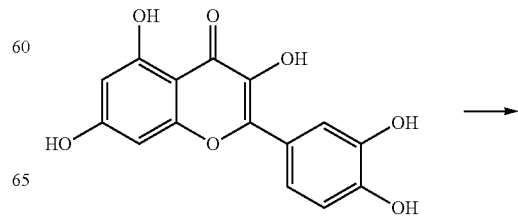

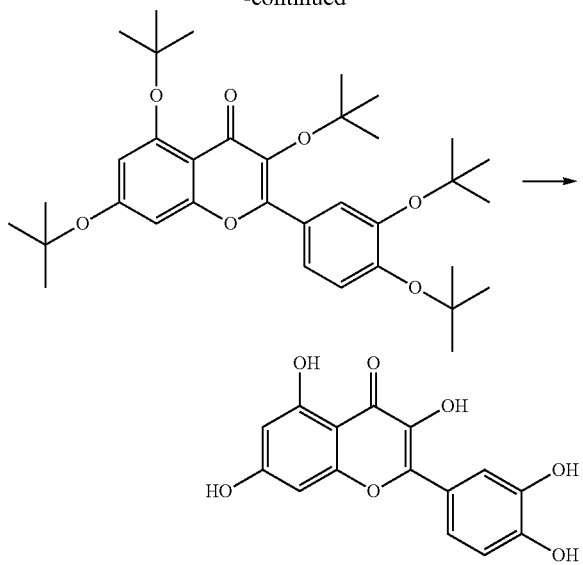

Procedure 4

In a reaction chamber, a flavonoid derivative (e.g. the one shown in example 1) undergoes a chemical reaction in the presence of suitable reagents, such as: $BCl_3$, $CH_2Cl_2$; at a temperature of—e.g. 0° C., resulting in release of structure modification in sufficient time (e.g. 5 minutes).

Procedure 4:

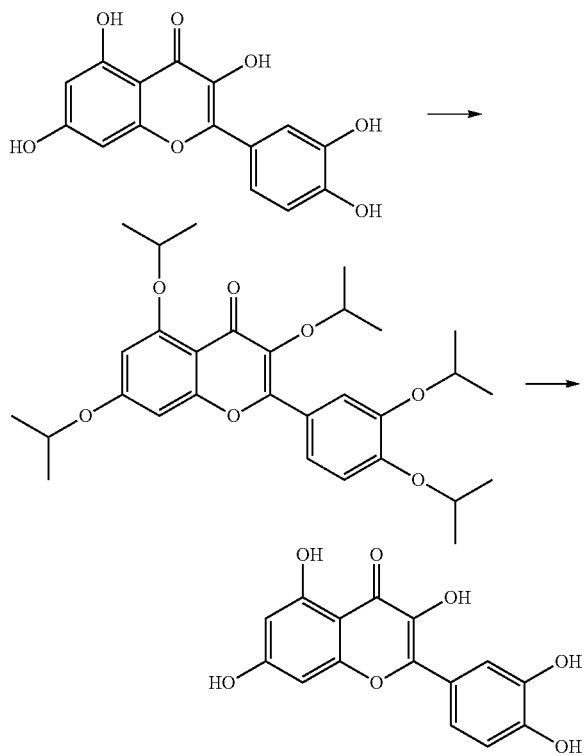

Of course, also other known techniques for the removal of protecting groups can be employed, such as the use of fluoride salts (e.g. TBAF, tetrabutyl ammonium fluoride) in combination with an aqueous work-up and organic solvent extraction for the removal of silyl groups. As such techniques are part of common knowledge in the field of organic chemistry, the skilled person can easily choose appropriate reactions and reaction conditions in view of the flavonoid derivative that is to be deprotected.

Procedure 5

In a round-bottomed flask, a flavonoid derivative (e.g. the ones shown in example 3 and 4) undergoes a chemical reaction in the presence of suitable reagents, such as: Potassium carbonate, in a mixture of tetrahydrofuran-water at reflux for 2 hours, resulting in release of structure modification.

Procedure 6

In a round-bottomed flask, a flavonoid derivative (e.g. the one shown in example 5) undergoes a chemical reaction in the presence of suitable reagents, such as: tetrabutyl ammonium fluoride, in tetrahydrofuran at reflux for 2 hours, resulting in release of structure modification.

Detection

The marker in the fuel is detected by transforming the marker (flavonoid derivative) into a flavonoid or a less hydrophobic flavonoid derivative by removing some or all of the structure modifications, as outlined above, and the resulting species is then detected by a suitable device. This may for instance be achieved as follows:

Within a Lab-on-a-chip (LOC), a specific chemical reaction leads to partial or complete release of the modifications introduced in the flavonoid structure in order to restore its electrochemical activity. The chemical reaction is followed by flavonoid separation, e.g. by precipitation (separation step). Within the LOC, then the detection of a flavonoid (qualitative and/or quantitative analysis) is performed on e.g. a carbon or metal-based (preferably microelectro-array) working electrode, using one of a standard electrochemical method.

The detection may be controlled with a smartphone coupled to a portable potentiostat, or an assembly of a potentiostat/galvanostat and a LOC. If desired, the test results may then be sent to a central control system.

Electrochemical Detection of Flavonoids, e.g. in LOC

The detection (qualitative and/or quantitative analysis) of electrochemically active flavonoids or flavonoid derivatives (i.e., being able to undergo oxidation and/or reduction) is performed in a three-electrode electrochemical compartment, using one of a standard electroanalytical method (voltammetric, amperometric or potentiometric).

Electroanalytical methods are class of techniques in analytical chemistry which study an analyte by measuring the potential (volts) and/or current (amperes) in an electrochemical cell. Both the qualitative and quantitative analysis can be obtained by analyzing the signal (current/or potential) obtained during the measurement. The intensity of the signal depends strongly on the concentration of the analyzed species (obtained from the marker), their reactivity as well as on the working electrode surface and may vary between nanoamperes and miliamperes for the potential range between −3 volts up to +3 volts.

Voltammetry is a category of electroanalytical methods in which information about an analyte is obtained by measuring the current as the potential is varied. The obtained curves (current in function of potential) give information on chemical processes (e.g., oxidation, reduction) occurring during the detection. The intensity of the signal, the shape of peaks and their position allow the qualitative and quantitative analysis of species of interests.

During voltammetric detection, the potential is varied either step by step or continuously, and the actual current value is measured as the dependent variable. Several voltammetric methods exist, depending on how the potential is applied: Linear Sweep Voltammetry, Cyclic Voltammetry, Square Wave Voltammetry, Differential Pulse Voltammetry, Normal Pulse Voltammetry, Differential Normal Pulse Voltammetry . . . etc.

Amperometry is a category of electroanalytical methods in which information about analyte is obtained by measuring a current as a function of an independent variable that is, typically, time or electrode potential. Several amperometric techniques exist depending on the operation mode: Chronoamperometry, Fast Amperometry, Pulsed Amperometry . . . etc.

Potentiometry is a category of electroanalytical methods in which information about analyte is obtained by measuring the potential of the electrochemical cell under static conditions. Several potentiometric techniques exist depending on operation mode: Chronopotentiometry, Linear Sweep Potentiometry, Cyclic Potentiometry, Fast Potentiometry . . . etc.

The technical details of abovementioned standard electrochemical methods could be found in a book of Allen J. Bard and Larry R. Faulkner (Authors), Electrochemical Methods: Fundamentals and Applications; ISBN-13: 978-0471043720.

Potentiometric methods require use of a galvanostat whereas voltammetric and amperometric methods require use of a potentiostat.

In LOC (FIGS. 1, 2, 3, 4) the electrochemical detection of a marker (electrochemically active flavonoid) is performed in a detection chamber [120] whereas electrochemical detection of a background signal is performed in detection chamber [220].

The electrochemical reactions (and abovementioned electrochemical methods) are controlled using a potentiostat or potentiostat/galvanostat, preferably a hand-held, portable device (i.e. potentiostat EmStat3 of PalmSens or bipotentiostat/galvanostat μStat400 of DropSens).

Potentiostat is the electronic hardware required to control a three electrode electrochemical cell (including a working electrode, a reference and a counter electrode). In other words, potentiostat is a control and measuring device used for most electrochemical experiments related to redox chemistry (oxidation/reduction) and other chemical phenomena.

Bipotentiostat or polypotentiostat are potentiostats capable of controlling more than 1 working electrode during the electrochemical experiment.

Potentiostat comprises an electric circuit which controls the potential across the cell by sensing changes in its resistance, varying accordingly the current supplied to the system: a higher resistance will result in a decreased current, while a lower resistance will result in an increased current, in order to keep the voltage constant as described by Ohm's law.

Galvanostat (or amperostat) is a control and measuring device capable of keeping the current through an electrochemical cell.

Therefore, potentiostat/galvanostat in its potentiostatic mode controls the potential of the counter electrode against the working electrode so that the potential difference between the working electrode and the reference electrode is well defined, and correspond to the value specified by the user. In galvanostatic mode, the current flow between the working electrode and the counter electrode is controlled. The potential difference between the reference electrode and working electrode and the current flowing between the counter electrode and working electrode are continuously monitored.

The electrochemical cell compartment comprises a reference, a counter, and a working electrode.

The working electrode is the electrode in an electrochemical system on which the reaction of interest is occurring. The working electrode can be a conventional-sized planar electrode (typically radius 1 mm or greater) or microelectrode (typically radius smaller than 50 micrometers). Preferably the working electrode is a microelectrode-array consisting of many individual but electrically connected microelectrodes, distributed randomly or arranged in a periodic (e.g., hexagonal or square) array.

Optionally, the working electrode could be in interdigitated configuration. In this case, the working electrode consists of two individually addressable arrays of microelectrodes with an interdigitated approach. Such configuration requires using a bipotentiostat to control electrochemical reactions.

The working electrode could be made of metal (platinum, gold, silver, palladium, copper, nickel . . . etc) or carbon based material (glassy carbon, graphite, mesoporous carbon, doped diamond . . . etc). The surface of the working electrode could be nanostructured (e.g., using nanotubes, nanofibers, nanowires, nanoparticles . . . etc.) or functionalized with electrochemical mediators in order to enhance electrochemical active area and/or electronic transfer properties.

The counter electrode (or auxiliary electrode) is an electrode which is used to close the current circuit in the electrochemical cell. It is usually made of an inert material (e.g. platinum, gold or graphite) and usually id does not participate in the electrochemical reaction.

The reference electrode is an electrode which has a stable and well-known electrode potential and it is used as point of reference in the electrochemical cell for the potential control and measurement.

In LOC/Electrolytic Solution

An electrolytic solution (present in chamber 203 in FIGS. 1 and 2, and 220 in FIG. 3) for measuring background signal contains the conductive agent introduced to enable electrochemical detection. Typically, an electrolytic solution should contain salt, acid or base, for example: sodium chloride NaCl, sodium nitrate $NaNO_3$, potassium chloride KCl, sodium perchlorate $NaClO_4$, perchloric acid $HClO_4$, sodium hydroxide NaOH, potassium hydroxide, chloric acid $HClO_3$ . . . etc, typically in the concentration range of 0.01M to 1M.

Electrolytic solution (present in chamber 102 in FIG. 1, 103 in FIG. 2, 120 in FIG. 3, and 100 in FIG. 4) contains a conductive agent (as above) and additionally contains the reactants to restore electrochemical activity of flavonoids.

Now there will be described preferable embodiments of LOC designs in conjunction with FIGS. 1 to 4. FIG. 1 shows a first embodiment of a design of a "reaction chamber" LOC, wherein the MEMS size is approximately 20 mm×17 mm. The marker detection can be performed as follows: In a first phase fuel and reactant can be introduced in the reaction chamber 100 through the inlet 101 and electrolytic solution can be introduced in the electrolytic solution chamber 102 through the inlet 102. If the reactant is already present inside the reaction chamber 100, only fuel has to be introduced through the inlet 101. In a phase 2, the reaction chamber 100 can be heated up to the reaction temperature, and then be cooled (actively or passively by switching off any heat source) to restore the marker electrochemical activity. In a phase 3 pressure can be applied in the inlet 301 to move both the fuel and the electrolytic solution, through the mixing channel 110. During the laminar flow of the two fluids "side by side" in the mixing channel 110, the hydrophilic flavonoids can move from the fuel to the electrolytic solution. At the end of the mixing channel 110, the electrolytic solution can be driven in the detection chamber 120, which has a hydrophilic floor surface. In a phase 4, electrochemical detection of Flavonoids can be carried out in an electrochemical cell compartment comprising a counter electrode 121, a working electrode (microelectrode-array) 122, and a reference electrode 123 using one of a standard electroanalytical method. The temperature of the cell can be maintained within a desired range by means of a heater 224.

A Blank Analysis can be performed in phases 1 to 3 as follows: In a phase 1, fuel is introduced in the fuel chamber 200 through the inlet 201 and the electrolytic solution is introduced in the electrolytic solution chamber 203 through the inlet 202. In a phase 2a pressure is applied in inlet 301 to move both the fuel and the electrolytic solution, through the mixing channel 210. At the end of the mixing channel 210, the electrolytic solution will be driven in the detection chamber 220. In a phase 3 background electrochemical analysis can be carried out in an electrochemical cell compartment comprising a counter electrode 221, a working electrode (microelectrode-array) 222, and a reference electrode 223 using one of a standard electroanalytical method. The temperature of the cell can be maintained within a desired range by means of a heater 224.

In general, a detection device of an embodiment of the present invention may further comprise a controller that is configured to control the fluid flow and the temperature for performing any method embodiment as part of the present disclosure. Specifically, the controller may operate valves, pumps, pressurizers, heating elements, cooling elements, and the like so as (1) mix a flavonoid derivative with an electrolytic solution to produce a mixture; (2) heat and then cool the mixture to change the electrochemical activity and produce an electrochemically more active flavonoid or flavonoid derivative; (3) separate said obtained electrochemically more active flavonoid or flavonoid derivative from the liquid, and (4) perform an electrochemical analysis of the obtained electrochemically more active flavonoid or flavonoid derivative. The latter may in particular be performed so as to obtain an output indicating an authenticity of a liquid, based on the contents of corresponding flavonoid derivatives.

Figure 2:
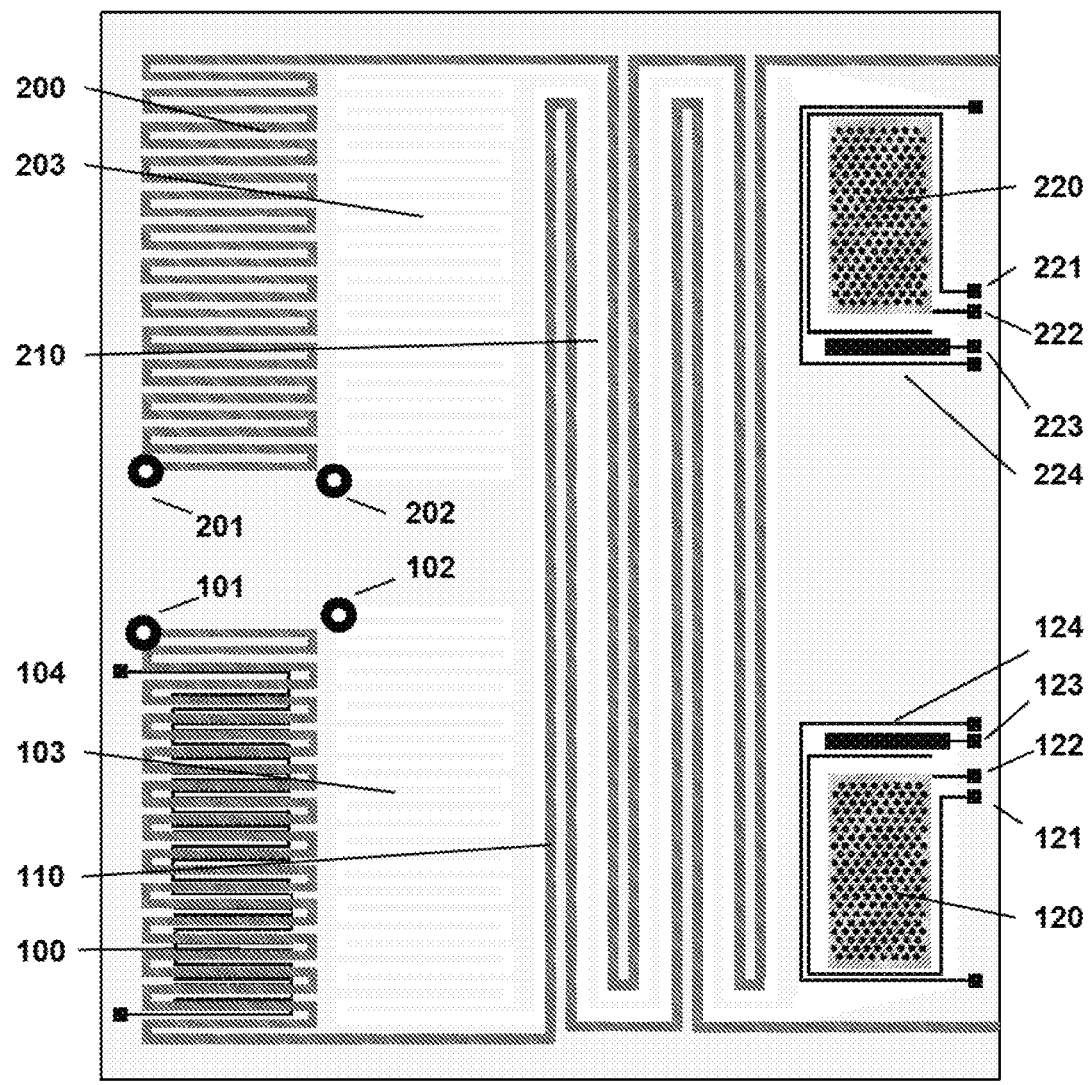
FIG. 2 shows a second embodiment of a design of a reaction chamber LOC.

FIG. 2 shows a second embodiment of a design of a "reaction channel" LOC, wherein the MEMS size is approximately 20 mm×17 mm. The marker detection can be performed as follows: In a phase there can be introduced at the same time the fuel with the reactant in the reaction channel 100 through the inlet 101 and the electrolytic solution in the electrolytic solution channel 103 through the inlet 102, and a pressure can be applied to move the fluids along their channels 100 and 103 up to the mixing channel 110 and the detection chamber 120. In a phase 2 the reaction channel 100 can be heated up to the reaction temperature, and then can be cooled (actively or passively by switching off any heat source). The marker electrochemical activity can be restored during its flow through the reaction channel 100. In a phase 3, the fuel with the re-activated marker and the electrolytic solution can reach at the same time the inlet of the mixing channel 110 and during their "side by side" flow, the hydrophilic flavonoids can move from the fuel to the electrolytic solution. At the end of the mixing channel 110, the electrolytic solution will be driven in the detection chamber 120, which has a hydrophilic floor surface. In a phase 4, Flavonoids electrochemical detection can take place in an electrochemical cell compartment comprising a counter electrode 121, a working electrode (microelectrode-array) 122, and a reference electrode 123 using one of a standard electroanalytical method. The temperature of the cell can be maintained within a desired range by means of a heater 224.

A Blank Analysis can be performed in phases 1 to 3 as follows: In a phase 1, there can be introduced at the same time the fuel in the fuel channel 200 through the inlet 201 and the electrolytic solution in the electrolytic channel 203 through the inlet 202, and a pressure can be applied to move the fluids along the channels 200 and 203 up to the mixing channel 210 and the detection chamber 220. In a phase 2, the electrolytic solution can be driven at the end of the mixing channel 210 in the detection chamber 220. In a phase 3 background Electrochemical Analysis can take place in an electrochemical cell compartment comprising a counter electrode 221, a working electrode (microelectrode-array) 222, and a reference electrode 223 using one of a standard electroanalytical method. The temperature of the cell can be maintained within a desired range by means of a heater 224.

Figure 3:
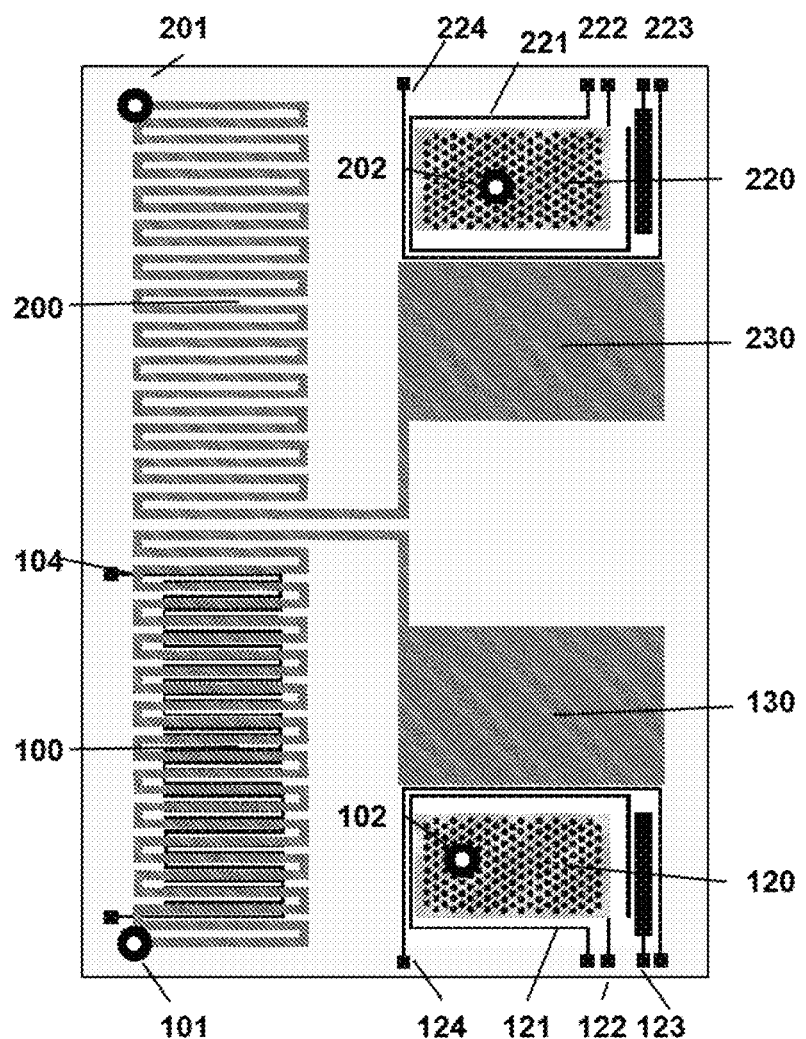
FIG. 3 shows a third embodiment of a design of a reaction chamber LOC.

FIG. 3 shows a third embodiment of a design of a "service chamber" LOC, wherein the MEMS size is approximately 10 mm×17 mm. The marker detection can be performed as follows: In a phase 1, electrolytic solution can be introduced in the detection chamber 120 through the inlet 102. The hydrophilic floor surface of the detection chamber 120 and the hydrophobic floor surface of the neighboring service chamber 130 can constrain the electrolytic solution in the detection chamber 130. In a phase 2, fuel with the reactant can be introduced in the reaction channel 100 through the inlet 101, and a pressure can be applied to move the fluid along the reaction channel 100 up to the service chamber 130. In a phase 3, the reaction channel 100 can be heated up to the reaction temperature, and can then be cooled (actively or passively by switching off any heat source). The marker electrochemical activity can be restored during its flow through the reaction channel 100. In a phase, the fuel with the re-activated marker can reach the service chamber 130 where it can stay in contact with the electrolytic solution as long as the hydrophilic flavonoids will move from the fuel to the electrolytic solution. In a phase 4, Flavonoids electrochemical detection can take place in an electrochemical cell compartment comprising a counter electrode 121, a working electrode (microelectrode-array) 122, and a reference electrode 123 using one of a standard electroanalytical method. The temperature of the cell can be maintained within a desired range by means of a heater 224.

A Blank Analysis can be performed in phases 1 to 3 as follows: In a phase 1, electrolytic solution can be introduced in the detection chamber 220 through the inlet 202. The hydrophilic floor surface of the detection chamber 220 and the hydrophobic floor surface of the neighboring service chamber 230 can constrain the electrolytic solution in the detection chamber 220. In a phase 2, fuel can be introduced in fuel channel 200 through the inlet 201, and a pressure can be applied to move the fluid along the channel 200 up to the service chamber 230. In a phase 3, the fuel can reach the service chamber 230 and can stay in contact with the electrolytic solution in detection chamber 220 for a time during which hydrophilic molecules could move from the fuel to the electrolytic solution. In a phase 4 background electrochemical analysis can take place in an electrochemical cell compartment comprising a counter electrode 221, a working electrode (microelectrode-array) 222, and a reference electrode 223 using one of a standard electroanalytical method. The temperature of the cell can be maintained within a desired range by means of a heater 224.

Figure 4:
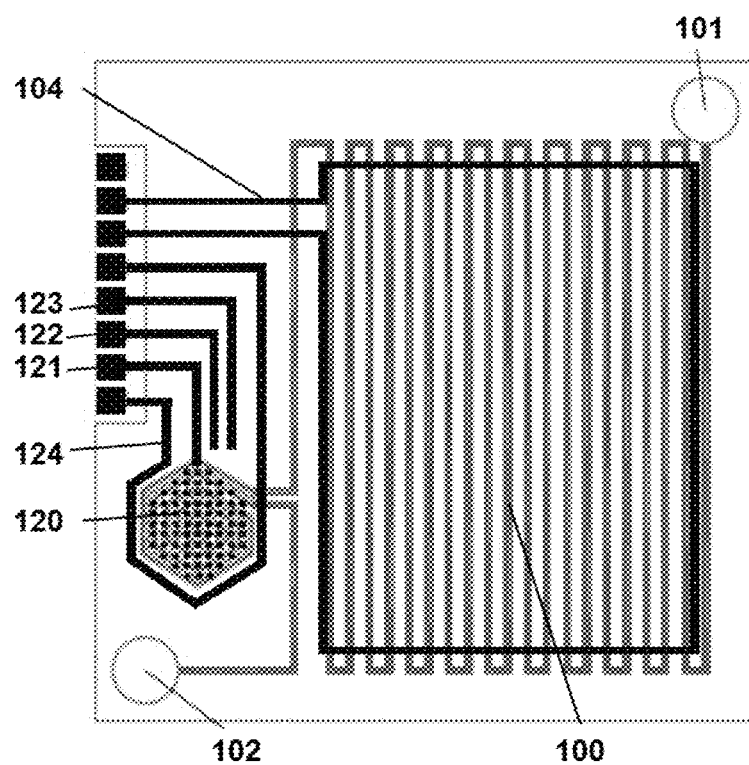
FIG. 4 shows a Flow on water MEMS layout.
Figure 5:
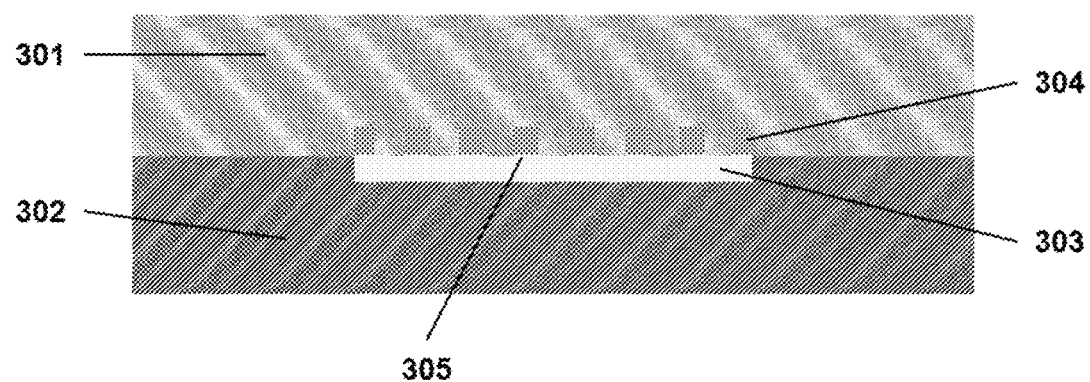
FIG. 5 shows a schematic cross-sectional view of the detection chamber 120 shown in FIG. 4.

FIGS. 4 and 5 show a fourth embodiment of a design of a "flow on water" LOC. The marker detection can be performed as follows: In a phase 1, fuel can be introduced with reactant in reaction channel 100 through the inlet 101, and a pressure can be applied to move the fluid along the reaction channel 100 up to the detection chamber 120. In a phase 2, the reaction channel 100 can be heated up to the reaction temperature, and it can then be cooled (actively or passively by switching off any heat source). The electrochemical activity can be restored during the flow through the reaction channel 100. In a phase 3, the fuel with the re-activated marker (i.e. the partially or fully de-derivatized marker) can reach the detection chamber 120 and can flow through its dedicated channel over the electrolytic solution. This effect is due both to the lower specific weight of fuel with respect to the electrolytic solution and to the wetting properties of the detection chamber surfaces: hydrophobic on the top (channel ceiling and walls) and hydrophilic on the bottom (electrolytic solution). During the fuel flow over the electrolytic solution the hydrophilic de-derivatized marker (e.g. flavonoid) will move from the fuel to the electrolytic solution. In a phase 4, the electrochemical detection of the partially or fully de-derivatized marker (e.g. of the flavonoid) can take place in an electrochemical cell compartment comprising a counter electrode 123, a working electrode (microelectrode-array) 121, and a reference electrode 122 using one of a standard electroanalytical method. The temperature of the cell can be maintained within a desired range by means of a heater 224. A schematic cross-sectional view of the detection chamber 120 is shown in FIG. 5.

According to a further embodiment of the present invention, an integration of a mobile phone or, generally, a combination with a mobile electronic device, such as a smartphone, a personal digital assistant (PDA), or the like, is envisaged. In such embodiments, to enable flavonoid detection, the LOC is connected to a potentiostat/galvanostat and a mobile (smart) phone or device. A corresponding application (software running on the phone/device) can be configured to communicate with a potentiostat, via a USB or wireless connection, such as a Bluetooth™ or WLAN dongle, and to control the detection process in the LOC according, for example, the above described processing phases. The detection results (qualitative and quantitative results) can then also be sent to a central control system/server by means of the networking and communication capabilities of the mentioned mobile phones/devices. Generally, the detection device can be implemented, at least in part, as a lab on chip (LOC) detection device.

LOC ⟷ Potentiostat/Galvanostat ⟵⋯⟶ Smartphone

DESCRIPTION OF DRAWINGS RELATED TO LOC DESIGN/LEGEND

FIG. 1. "Reaction Chamber" MEMS Layout
Marker Detection:
100: Reaction chamber
101: (Fuel+Reactant) Inlet
103: Electrolytic Solution Chamber
102: Electrolytic Solution Inlet
104: Heater
Blank Analysis:
200: Fuel chamber
201: Fuel Inlet
203: Electrolytic Solution Chamber
202: Electrolytic Solution Inlet
301: Pressure Inlet.
110,210: mixing channels
120,220: Detection chambers
122,222: Micro-array Working Elect.
121,221: Counter Elect.
123,223: Reference Elect.
124,224: Heater
FIG. 2. "Reaction Channel" MEMS Layout
Marker Detection:
100: Reaction channel
101: (Fuel+Reactant) Inlet
103: Electrolytic Solution Channel
102: Electrolytic Solution Inlet
104: Heater
Blank Analysis:
200: Fuel channel
201: Fuel Inlet
203: Electrolytic Solution Channel
202: Electrolytic Solution Inlet
110,210: mixing channels
120,220: Detection chambers
122,222: Micro-array Working Elect.
121,221: Counter Elect.
123,223: Reference Elect.
124,224: Heater
FIG. 3. "Service Chamber" MEMS Layout
Marker Detection:
100: Reaction channel
101: (Fuel+Reactant) Inlet
102: Electrolytic Solution Inlet
104: Heater
130: Service chamber
Blank Analysis:
200: Fuel channel
201: Fuel Inlet
202: Electrolytic Solution Inlet
230: Service Chamber
110,210: mixing channels
120,220: Detection chambers
122,222: Micro-array Working Elect.
121,221: Counter Elect.
123,223: Reference Elect.
124,224: Heater
FIG. 4. "Flow on Water" MEMS Layout
Marker Detection:
101: (Fuel+Reactant) Inlet
102: (Fuel+Reactant) Outlet
100: Reaction channel
Heater reaction channel for Reaction Temperature Control
120: Detection chambers
Electrolytic solution on the floor of the detection chamber.
121: Micro-array Working Electrode (WE)
122: Counter Electrode (CE)
123: Reference Electrode (RE)
124: Heater
FIG. 5. A Scheme of Cross-section View of the Detection Chamber [120] in FIG. 4
301: Top of the LOC.
302: Bottom of the LOC.
303: Electrolytic solution inside the detection chamber.
304: Fuel inside the channel
305: Contact surface between fuel and electrolytic solution.

The invention claimed is:
1. A composition that is a liquid at 20° C. and 1 atm pressure, comprising
  a) an authentication marker being a flavonoid derivative obtainable by modifying hydroxyl groups of a fla- vonoid with organic groups, a concentration of the flavonoid derivative being 100 ppm by weight or less, and b) an organic substance in an amount of 90% by weight or more, wherein the authentication marker is not naturally occurring in the compostion.

2. The composition that is a liquid at 20° C. and 1 atm pressure according to claim 1, wherein the composition is a fuel and wherein the organic substance is present in an amount of equal to or greater than 95% by weight and is one or more hydrocarbons having 6 to 22 carbon atoms, methanol or ethanol.

3. The composition according to claim 1, wherein the flavonoid derivative loses some or all of the modifying organic groups upon heating to a temperature of 50° C. or higher.

4. The composition according to claim 1, wherein the flavonoid derivative obtainable by modifying the hydroxyl groups of a flavonoid with organic groups is represented by any of the following formulae:

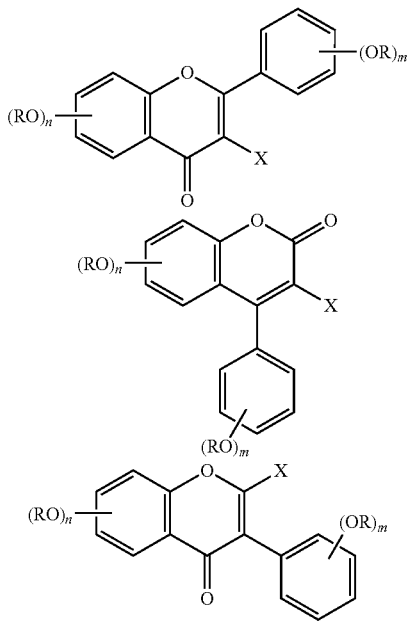

where X represents H or OR;

n represents an integer of 0 to 4, and m represents an integer of 0 to 5, provided the sum of m and n is 2 or more, several R in one molecule can be the same or different, and each R can be

H, a branched, linear or cyclic alkyl group having 1 to 50, a C(=O)-alkyl group, wherein the alkyl group is defined as above, a trialkylsilyl group wherein the alkyl groups each are independently a branched, linear or cyclic alkyl group having 1 to 50, a diarylalkylsilyl group having two aryl groups and one alkyl group wherein the alkyl group is a branched, linear or cyclic alkyl group having 1 to 50, and the aryl groups are each independently aromatic rings having 6 to 10 carbon atoms, a dialkylarylsilyl group having one aryl group and two alkyl groups, wherein the alkyl groups and the aryl groups are defined as above for the diarylalkylsilyl group, an allyl group, a methylene alkylether group, wherein the alkyl group is defined as above, or a tetrahydropyranyl group, with the proviso that at least one of the R groups does not represent hydrogen.

5. A method for authenticating the genuineness and/or origin of the composition according to claim 1, comprising the steps of mixing the composition comprising the flavonoid derivative with an electrolytic solution to produce a mixture;

heating and then cooling the mixture to produce a flavonoid or flavonoid derivative that is electrochemically more active as compared to the flavonoid derivative that is mixed with an electrolytic solution to produce the mixture;

separating said obtained electrochemically more active flavonoid or flavonoid derivative from the mixture, and performing electrochemical analysis of the obtained electrochemically more active flavonoid or flavonoid derivative.

6. The method according to claim 5, wherein the composition that is a liquid is a fuel and wherein a concentration of the marker is equal to or less than 10 ppm by weight.

7. The method according to claim 5, wherein the method is implemented in a portable device.

8. The method according to claim 5, wherein the separation of the obtained electrochemically more active flavonoid or flavonoid derivative from the composition that is a liquid is achieved with a flow side by side in a mixing channel where also the electrolytic solution is flowing.

9. The method according to claim 5, wherein the method is performed in a lab-on-chip detection device.

10. The composition that is a liquid at 20° C. and 1 atm pressure according to claim 1, wherein the flavonoid derivative obtainable by modifying the hydroxyl groups of a flavonoid with organic groups contains a structural unit derived from quercetin or morin.

11. A detection device configured to fully or partially de-derivatize the flavonoid derivative comprised in the composition according to claim 1 and to separate said partially or fully de-derivatized flavonoid from said composition, comprising:

a reaction chamber for holding a reactant and for receiving said composition;

a first entry and a microfluidic channel for introducing an amount of said composition into the reaction chamber;

a heater for heating up the reaction chamber to a reaction temperature;

an electrolytic solution chamber for holding an electrolytic solution;

a second entry for introducing an amount of said electrolytic solution into the electrolytic solution chamber;

a mixing channel configured to establish a laminar side-by-side flow of the mixture of said composition and reactant from the reaction chamber and the electrolytic solution from the electrolytic solution chamber; and a detection chamber arranged at the end of said mixing channel and having electrodes for electrochemical analysis.

12. The detection device of claim 11, further comprising an active cooling element for cooling said reaction chamber.

13. The detection device of claim 11, wherein the detection chamber comprises hydrophilic surface.

14. The detection device of claim 11, wherein the detection chamber comprises a working electrode, a counter electrode, and a reference electrode.

15. The detection device of claim 14, wherein the working electrode comprises a microelectrode array.

16. The detection device of claim 11, further comprising a controller configured to control fluid flow and temperature.

17. A system comprising the composition according to claim 1 and a detection device configured to fully or partially de-derivatize the flavonoid derivative comprised in the composition and to separate said partially or fully de-derivatized flavonoid from said composition, comprising:

a reaction chamber for holding a reactant and for receiving said composition;

a first entry and a microfluidic channel for introducing an amount of said composition into the reaction chamber;

a heater for heating up the reaction chamber to a reaction temperature;

an electrolytic solution chamber for holding an electrolytic solution;

a second entry for introducing an amount of said electrolytic solution into the electrolytic solution chamber;

a mixing channel configured to establish a laminar side-by-side flow of the mixture of said composition and reactant from the reaction chamber and the electrolytic solution from the electrolytic solution chamber; and a detection chamber arranged at the end of said mixing channel and having electrodes for electrochemical analysis.

18. The system according to claim 17, wherein the flavonoid derivative contains a structural unit derived from quercetin or morin.

19. The method according to claim 5, wherein the flavonoid derivative obtainable by modifying the hydroxyl groups of a flavonoid with organic groups contains a structural unit derived from quercetin or morin.

* * * * *